United States Patent
Ewerlöf

(12) 
(10) Patent No.: US 6,767,337 B1
(45) Date of Patent: Jul. 27, 2004

(54) INFUSION APPARATUS FOR USE WITH AN INFUSION BAG

(75) Inventor: Göran Ewerlöf, Lidingo (SE)

(73) Assignee: Gepro Produktutveckling AB (SE)

( * ) Notice: Subject to any disclaimer, the term of this patent is extended or adjusted under 35 U.S.C. 154(b) by 63 days.

(21) Appl. No.: 10/110,658

(22) PCT Filed: Oct. 11, 2000

(86) PCT No.: PCT/SE00/01963

§ 371 (c)(1),
(2), (4) Date: Aug. 13, 2002

(87) PCT Pub. No.: WO01/26715

PCT Pub. Date: Apr. 19, 2001

(30) Foreign Application Priority Data

Oct. 13, 1999 (SE) .............................................. 9903683

(51) Int. Cl.$^7$ ....................... A61M 31/00; A61M 37/00; A61M 1/00
(52) U.S. Cl. ......................... 604/153; 604/67; 604/132; 604/141
(58) Field of Search ................................ 604/131–135, 604/140–144, 67, 151, 153; 417/474–479

(56) References Cited

U.S. PATENT DOCUMENTS

| 4,460,358 | A |   | 7/1984  | Somerville et al. ......... 604/250 |
| 4,869,457 | A | * | 9/1989  | Ewerlof ...................... 251/6 |
| 5,348,539 | A |   | 9/1994  | Herskowitz .................. 604/141 |
| 5,411,482 | A | * | 5/1995  | Campbell .................... 604/153 |
| 5,472,420 | A |   | 12/1995 | Campbell .................... 604/67 |
| 6,398,760 | B1 | * | 6/2002 | Danby ........................ 604/132 |

FOREIGN PATENT DOCUMENTS

WO      9613288     5/1996

* cited by examiner

Primary Examiner—Brian L. Casler
Assistant Examiner—Catherine S. Williams
(74) Attorney, Agent, or Firm—Ostrolenk, Faber, Gerb & Soffen, LLP

(57) ABSTRACT

The invention relates to an infusion apparatus for use in combination with an infusion bag (10) comprising and/or being connectable with a conduit means (12) for transport of infusion liquid to a patient. The infusion apparatus comprises a first space (14) in which the infusion bag (10) is disposed. The infusion apparatus comprises also a second space (16). The volume of this second space (16) can be varied by supplying a pressure generating liquid to the second space (16). This change in volume of the second space (16) exerts a pressure on the infusion bag (10). The infusion apparatus comprises also a closing means (20) which exerts a load on the conduit means (12). If the pressure generating liquid exerts a pressure on the infusion bag (10) the load will decrease. This allows infusion liquid to leave the infusion bag (10) via the conduit means (12).

6 Claims, 3 Drawing Sheets

INFUSION APPARATUS FOR USE WITH AN INFUSION BAG

Figure 1:
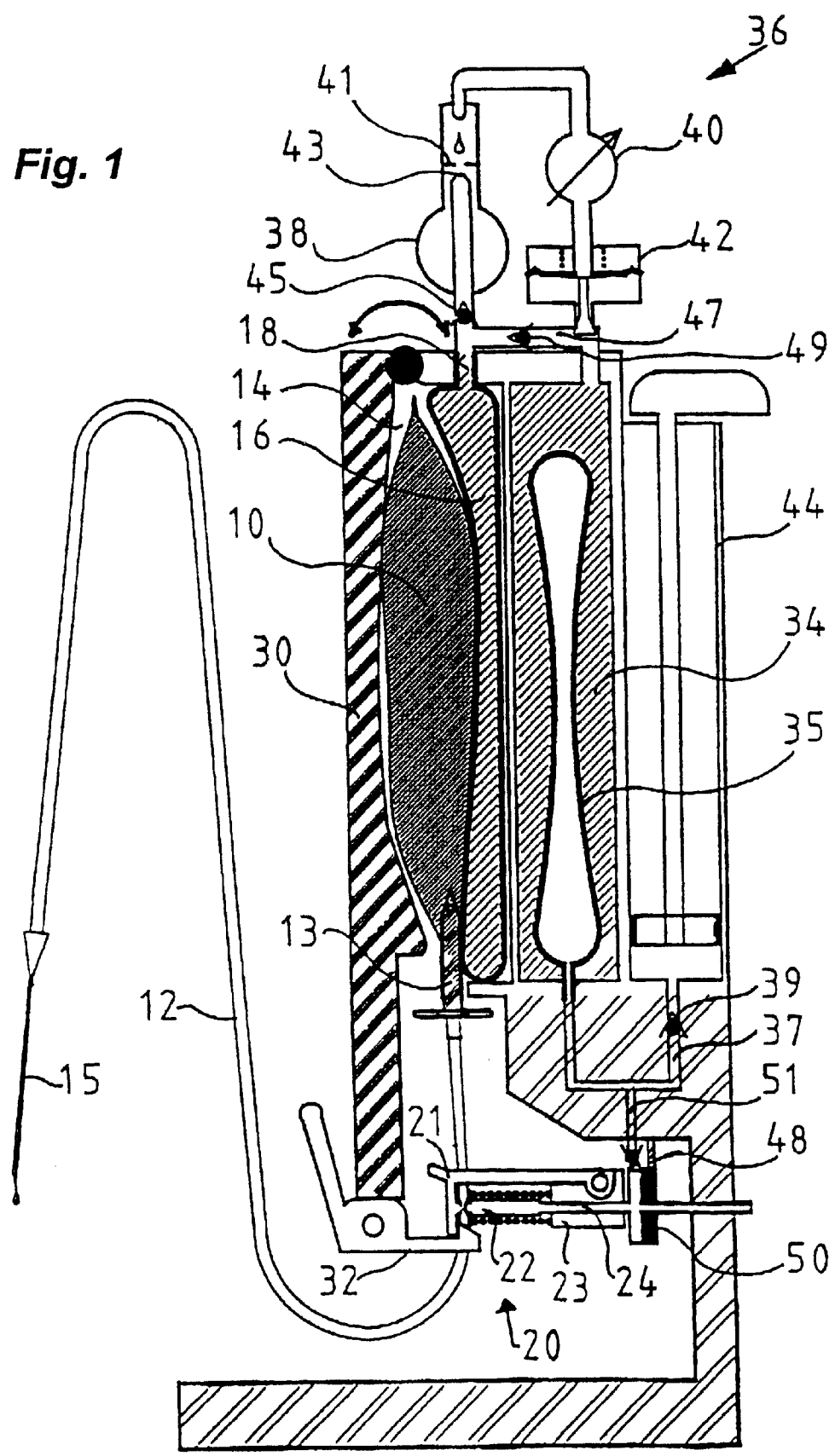

The present invention relates to an infusion apparatus for use with an infusion bag containing an infusion liquid, which comprises and/or is connectable with a conduit means for transport of infusion liquid to a patient, the infusion apparatus being of a type which comprises:

a first space in which the infusion bag is intended to be disposed, a second space of variable volume provided with an inlet through which a pressure generating liquid is supplied to the second space to change its volume, the first and second spaces being so arranged that the pressure generating liquid, by said change of volume, exerts a pressure on the infusion bag in the first space to make the infusion liquid leave the infusion bag via the conduit means. An infusion apparatus of this kind is known from U.S. Pat. No. 5,348,539. This document describes an infusion apparatus with a suitable space for comprising an infusion bag. A second space abuts the infusion bag. Into this second space a liquid, for instance, can be introduced by means of a pump system. When the liquid is introduced into the second space, the second space exerts a pressure on the infusion bag. Thereby infusion liquid is conducted out from the infusion bag. In order to supply a liquid to the second space the apparatus comprises a pump or relatively complicated design. Furthermore the apparatus comprises an electrically controlled control device. The apparatus, in addition, comprises various sensors. In case of excessive pressure in the second space the pump motor is switched off.

WO 96/13288 describes an infusion pump preferably driven by air. Alternatively a liquid can be used. A pump pumps air to a bladder which exerts pressure on an infusion bag. The apparatus also comprises a pressure sensor and a monitoring circuit.

The apparatus described in the aforementioned documents are of relatively complex design and comprise monitoring circuits and pressure sensors.

It is also known in health care that infusion liquid can be supplied to a patient directly from an infusion bag. In this case the infusion bag is placed on a higher level than the patient. By means of a tube originating at the infusion bag infusion liquid is transported by gravitation to a cannula connected to the patient. Such an arrangement often comprises a controllable clip arrangement attached to a tube to control the flow rate of the infusion liquid. The apparatus can also comprise a drip chamber to visualise the flow rate. With such an apparatus it is difficult to precisely control the flow rate of the infusion liquid.

In connection with infusion apparatus often relatively expensive disposable components have to be used.

In health care a large number of infusions are given. In certain infusions of such kind it is very important that the infusion liquid be supplied to the patient at a precisely controlled flow rate. When, for instance, certain drugs are administered to a patient by infusion it is often necessary to control the dosage precisely. Furthermore it is advantageous if the flow rate of the infusion liquid is independent of the relative height level of the infusion bag in respect of patient.

SUMMARY OF THE INVENTION

An object of the present invention is to provide an infusion apparatus which can be used with infusion bags containing an infusion liquid; the infusion apparatus should be relatively simple and cheap to manufacture while, at the same time, operating with a high degree of safety. Another object of the invention is that the infusion apparatus should be able to transport infusion liquid to a patient at a well-controlled flow rate. A further object of the invention is to avoid the use of expensive disposable components in connection with the infusion apparatus.

These objects of the invention are provided by an infusion apparatus of the kind disclosed in the introduction, the apparatus being characterised by comprising a closing means of a form and disposition to abut against and exert a load on the conduit means in such a manner that the infusion liquid does not flow out from the infusion bag when the pressure generating liquid is not exerting a pressure on the infusion bag, while said load diminishes when the pressure generating liquid is exerting a pressure on the infusion bag to make infusion liquid leave the infusion bag via the conduit means if the pressure generating liquid exerts at least a certain minimum pressure on the infusion bag.

When a pressure of a certain size is exerted on the infusion bag the load of the closing means on the conduit means thus decreases while infusion liquid leaves the infusion bag via the conduit means. An increase in pressure on the infusion bag results in a state of equilibrium which causes infusion liquid to be transported to the patient at a well-controlled flow rate. This makes the height level of the infusion bag in relation the patient to lack effect on the flow rate. It should be noted that the closing means might abut a tube extending from the infusion bag to the patient. It is also possible for the closing means to abut an outlet area forming a part of the infusion bag proper. In this patent application the term "infusion liquid" shall be understood in a broad sense and thus comprises, for example, also liquid or material carried in a liquid which is given to a patient by tube-feeding. The term also comprises blood which is given in blood transfusion.

According to a preferred embodiment of the invention the infusion apparatus comprises a supporting means arranged to abut the infusion bag when the infusion bag is disposed in the first space, the supporting element being arranged in such a way that, when the pressure generating liquid is exerting a pressure on the infusion bag the infusion bag will exert a pressure on the supporting means, the infusion apparatus comprising a connecting element for connecting the supporting means with the closing means, to make the load exerted by the closing means on the conduit means decrease when the infusion bag is exerting a pressure on the supporting means. Thus an increase of pressure on the infusion bag contributes, by assistance of the supporting means, to decrease the load of the closing means on the conduit means. This contributes to a state of equilibrium being reached between the pressure of the infusion liquid and the load on the closing means at a relatively small increase of pressure on the infusion bag. This results in the flow rate of the infusion liquid to the patient to be controlled with very high precision.

According to a further embodiment of the invention the closing means comprises a first portion and a second portion which, in combination, abut resiliently against and exert a load on the conduit means in such a manner, that the conduit means is clamped between the first and second portions while the connecting element connects the supporting means and the first portion in such a way that, when the pressure on the supporting means increases, the first portion is affected to move in a direction away from the second portion while the load exerted by the first and second portions on the conduit means decreases. This embodiment is a technically simple and well functioning application of the invention.

According to still another embodiment of the invention the infusion apparatus comprises a third space arranged to contain pressure generating liquid, the third space being connected with the second space by joining means for transport of the pressure generating liquid from the third space to the second space. Thus the infusion apparatus comprises the pressure generating liquid; therefore it is not necessary to supply this liquid to the infusion apparatus from an external source.

According to a further embodiment of the invention the connecting means comprises a drip chamber which allows visual control of the pressure generating liquid transported from the third to the second space. A person supervising the infusion apparatus thus can see by his/her own eyes at which flow rate the pressure generating liquid is being transported to the second space. Thereby an indication is indirectly obtained in regard of at what rate the pressure is being built up in the second space.

According to a further embodiment of the invention the infusion apparatus is designed in such a way, that, when the pressure generating liquid exerts a pressure on the infusion bag of a size that makes the infusion liquid leave the infusion bag via the conduit means, the flow rate of the pressure generating liquid in the drip chamber will correspond to the flow rate of the infusion liquid in the conduit means. This makes the visual control of the flow rate of the pressure generating liquid to constitute, at the same time, a visual control of the flow rate of infusion liquid to the patient. Thus the drip chamber can be arranged permanently in the infusion apparatus in a closed system for transport of pressure generating liquid from the third to the second space. Thus there is, for instance, no need for a further drip chamber to be arranged at the conduit means leading to the patient.

According to still a further embodiment of the invention the connecting means comprises a flow rate regulator to control the flow rate of the pressure generating liquid to the second space. Thereby the flow rate of the pressure generating liquid can be controlled with a high degree of precision. This makes the flow rate of the infusion liquid also to be controllable with precision.

According to still a further embodiment of the invention the connecting means comprises a pressure regulator disposed between the third space and the flow rate regulator to provide a constant pressure in the pressure generating liquid present at the side of the flow speed regulator to which pressure generating liquid is supplied from the third space. The existence of such a constant pressure does not change the flow rate of the pressure generating liquid provided that the flow rate regulator setting is not changed. A pressure regulator of this kind thus contributes to maintain a well-controlled flow rate of the infusion liquid.

According to a further embodiment of the invention the infusion apparatus comprises pressure generating means to generate a pressure at the pressure generating liquid present in the third space. Thereby a pressure of the pressure generating liquid thus can be built up. As a pressure generating means a hand-driven air pump can be used, for instance. The pressure generated in the pressure generating liquid in the third space should be high enough to make it exceed, during the entire infusion process, the target pressure exerted on the infusion bag.

According to a further embodiment of the invention the infusion apparatus comprises a pump unit arranged to pump the pressure generating liquid from the third space to the second space at a controlled pumping rate. This embodiment thus constitutes an alternative to putting the pressure generating liquid in the third space under pressure. By the pump unit pumping pressure generating liquid at a controlled pumping rate a controlled flow rate of infusion liquid to the patient is also obtained.

According to still a further embodiment of the invention the infusion apparatus comprises a safety function in regard of overpressure which, when a given pressure of the infusion liquid in the confusion bag is exceeded, prevents infusion liquid from being transported along the conduit means. Such a safety function in regard of overpressure, i.a., has the advantage that, should a blocking occur in the conduit means or in a cannula connected to a patient, the safety function in regard of overpressure will be trigged. Thereby the transport of infusion liquid is stopped.

According to still a further embodiment of the invention the second portion is connected to a frame portion of the infusion apparatus by means of a joining element in such a manner, that, when a force exceeding a certain level is exerted on the second portion in at least one direction, the second portion will disengage from the frame portion, the safety function in regard of overpressure being arranged to be exerted, in combination, by the supporting means, the connecting element, the first portion, the second portion, and the joining element in combination in such a way that, if the pressure on the supporting means exceeds a certain level in spite of the supporting means, by the connecting element, having affected the first portion to reduce the load on the conduit means, the supporting means, by the connecting element, the first portion and the joining element, causes the second portion to disengage from the frame portion, making the load on the conduit means to increase again while decreasing the pressure on the supporting means. According to this embodiment a well working, relatively simple safety function in regard of overpressure is obtained.

According to a further embodiment of the invention the joining element comprises a magnet. Such a magnet can, for instance, be a permanent magnet. The permanent magnet thus holds the second portion fixed in relation to the frame portion. When a force exceeding a certain level is exerted on the second portion, the second portion will disengage from the frame portion. By the connecting element being a magnet the safety function in regard of overpressure is obtained by simple means.

SHORT DESCRIPTION OF THE DRAWING

The invention will now be described in more detail by means of several embodiments and by reference to the attached figures.

Figure 2A:
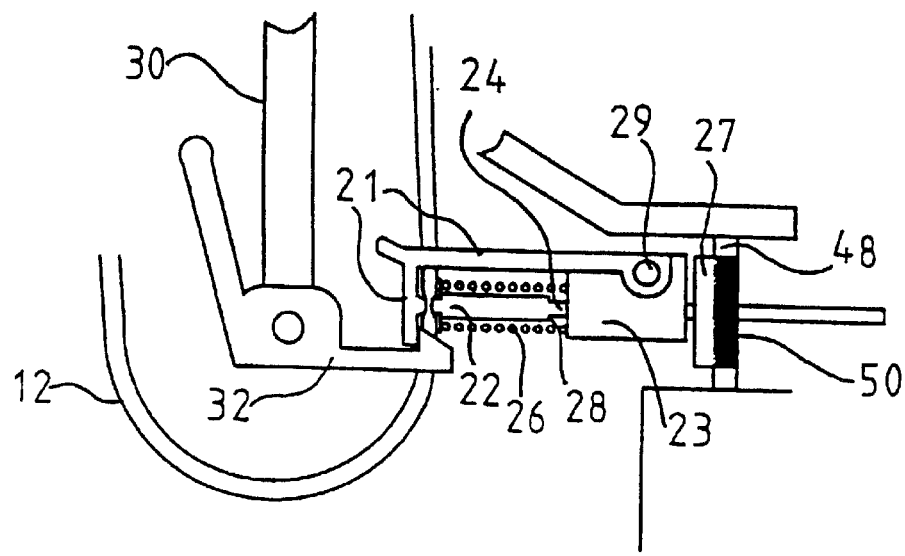
Figure 3:
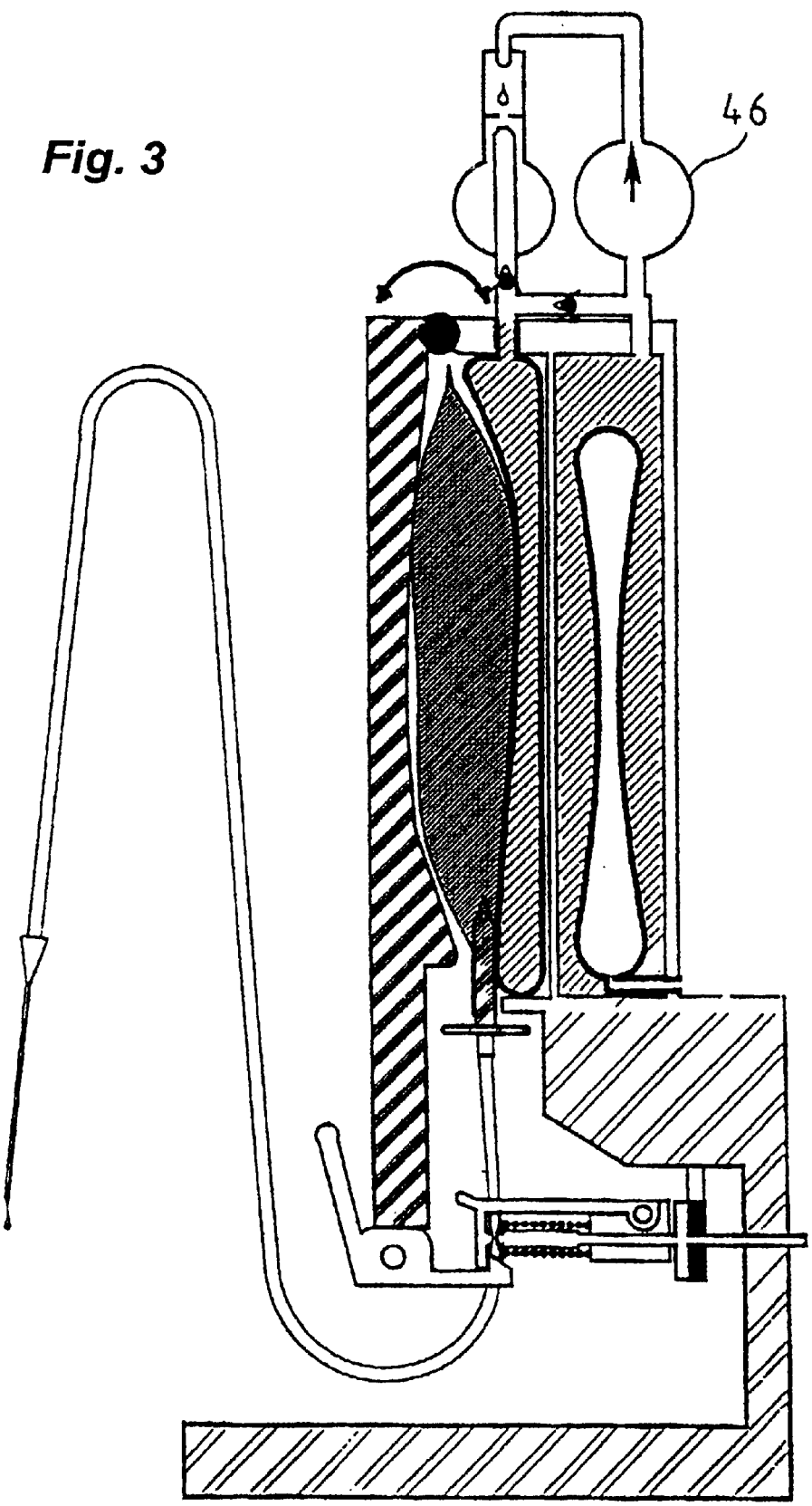

FIG. 1 shows schematically an embodiment of the invention;

FIGS. 2a, b and c show schematically an embodiment of a safety function in regard of overpressure which can be comprised by the infusion apparatus according to the invention;

FIG. 3 shows schematically an alternative embodiment of the invention.

DESCRIPTION OF PREFERRED EMBODIMENTS OF THE INVENTION

In the various figures elements corresponding to each other are identified by same reference numbers. All construction details thus will not be mentioned in connection with each figure.

FIG. 1 shows an example of an infusion apparatus according to the invention. The infusion apparatus is also called infusion pump. The infusion apparatus comprises a first space 14. This first space 14 is intended to comprise an infusion bag 10. Such an infusion bag 10 can contain various infusion liquids, for instance, a nutrition solution, blood or nutrients which shall be administered to a patient by, for example, tube feeding. The infusion bag can also contain medicines to be administered to a patient in precisely defined given doses. The infusion bag 10 comprises can be connected with a conduit means 12. The conduit means 12 can, for instance, be connected to the infusion bag 10 by means of an exit cannula 13 which, for instance, penetrates a membrane disposed in the infusion bag 10. The conduit means 12 is advantageously connected with an infusion cannula 14 which can be connected with a patient.

The infusion apparatus comprises also a second space 16. This second space 16 has a variable volume. The second space 16 is provided with an inlet 18 through which a pressure generating liquid can be supplied to the second space 16. The second space 16 can, for instance, be a rubber bladder. When a pressure generating liquid is supplied to the second space 16 the second space 16 will expand. Thereby a pressure is exerted on the infusion bag 10. Thus the pressure of the infusion liquid in the infusion bag 10 will increase too. The infusion apparatus comprises a closing means 20. The closing means 20 comprises a first portion 21 and a second portion 22. The first portion 21 and the second portion 22 abut in combination resiliently against and exert a load on the conduit means 12. By the conduit means 12 thus being clamped between the first 21 and second 22 portions, infusion liquid is prevented from flowing uncontrolled out from the infusion bag 10 even if the conduit means 12 and the infusion cannula 15 are disposed at a lower level than the infusion bag 10. When the pressure on the infusion bag increases, the load of the first 21 and second 22 portions on the conduit means 12 will however decrease, thereby allowing infusion liquid to leave the infusion bag via the conduit means 12.

The first portion 21 is connected with a first section 23 via a shaft 29 (see also FIG. 2). The first section 23 is glidably arranged in relation to a second section 24 forming a part of the second portion 22. The second portion 22 also comprises a stop washer 25. Between the stop washer 25 and the first section 23 is arranged a spring coil 26. This spring coil 26 exerts a load on the first section 23 in such a manner that the first section 23 is pushed in a direction away from the stop washer 25. Since the first section 23 is connected with the first portion 21 a force is also exerted on the portion 21. The conducting means 12 thus is clamped between the first 21 and the second 22 portions.

The infusion apparatus also comprises a third space 34. This third space 34 comprises a pressure generating liquid which can be transferred to the second space 16 via a connecting means 36. The infusion apparatus comprises pressure generating means 44 to generate pressure at the pressure generating liquid in the third space 34. The pressure generating means 44 can be a hand-driven air pump. The hand-driven air pump 44 is in communication with a second rubber bladder 35 via a first conduit 37. The first conduit 37 comprises a one-way valve 39 permitting air to be transported from the air pump 44 to the second rubber bladder 35 but not in the opposite direction.

The connecting means 36 comprises a pressure regulator 42, a flow rate regulator 40 and a drip chamber 38. The pressure regulator 42 provides a constant pressure in the pressure generating liquid disposed at the side of the flow speed regulator 40 to which pressure generator liquid is supplied from the third space 34. By means of the flow rate regulator 40 the flow rate of the pressure generating liquid to the second space 16 can be controlled. The pressure regulator 42 allows a constant flow rate of the pressure generating liquid to be obtained.

The drip chamber 38 allows visual control of the flow rate of the pressure generating liquid to the second space 16. As a pressure generating liquid water or a non-poisonous oil, for instance, can be used. The pressure generating liquid is preferably opaque, coloured and/or luminescent to make the flow rate in the drip chamber 38 distinct. In the drip chamber 38 a liquid level 41 is indicated. This liquid level 41 is situated above an inlet opening 43 through which the pressure generating liquid is conducted into the second space 16. The volume in the drip chamber 38 above the inlet opening 43 appropriately is substantially smaller than the volume in the drip chamber 38 below the level of the inlet opening 43. This guarantees that air is not led into the second space 16 even if the infusion apparatus is be turned up and down during an infusion process. The connecting means 36 comprises also a second one-way valve 45. Should air in spite of this reach the second space 16 it would thus do no damage. When the infusion bag 10 is changed in connection with new infusion the air will be led back to the third space 34 and occupy an space uppermost in this third space 34. From this position air will again be led to the drip chamber 38 at the start of the infusion process.

The apparatus also comprises a second conduit 47 extending from the second space 16 to the third space 34. The second conduit 47 comprises a third one-way valve 49.

The apparatus comprises a supporting means 30. In the embodiment shown the supporting means 30 is a lid. This lid is disposed to abut the infusion bag 10 when the infusion bag is disposed in the first space 14. When the pressure generating liquid in the second space 16 exerts a pressure on the infusion bag 10 the infusion bag 10 will exert a pressure on the lid 30. The lid 30 is connected with the first portion 21 of the closing means 20 via a connecting element 32. When the pressure on the lid 30 increases the connecting element 32 will pull the first portion 21 in a direction away from the second portion 22. Thereby the load exerted by the first 21 and the second 22 portions on the conduit means 12 is decreased. In this situation infusion liquid is allowed to leave the infusion bag 10 and to be led to a patient via the conduit means 12.

The infusion apparatus comprises also a safety function in regard of overpressure which prevents infusion liquid from being transported along the conduit means 12 should the pressure in the infusion bag 10 be too high. For this purpose the apparatus comprises a third section 27, suitably of metal, which is fixed at or forms a part of the second portion 22. A connecting element 50 in form of a magnet is connected with a frame portion 48 of the infusion apparatus. The magnet 50 can be fixed at the frame portion 48 while the third section 27 may be fixed at the second portion 22, or vice versa. The second portion 22 comprises a stop face 28. The first section 23, which is connected with the first portion 21, thus is allowed to glide in relation to the second section 24 until the first section 23 reaches the stop face 28. The apparatus comprises also a third conduit 51 extending from the first conduit 37. This third conduit 51 allows the pressure in the first conduit 37, and thus in the third space 34, to be decreased when the safety function in regard of excessive pressure is triggered.

The function of the invention will now be described.

An infusion bag 10 with a conduit means 12 connected to it is disposed in the first space 14. The lid 30 is closed and the connecting element 32 is connected with the first portion 21. By the first 21 and the second 22 portions clamping the conduit means 12 by means of a spring coil 26 infusion liquid is prevented from flowing through the conduit means 12. When the lid 30 is closed the second space 16 is compressed which causes the pressure generating liquid to flow from the second space 16 to the third space 34 via the second conduit 47.

Thereafter the second rubber bladder 35 is put under pressure by means of the air pump 44. Thereby the pressure in the third space 34 is increased. During the entire infusion process the pressure in the third space 34 has to be sufficiently high to press infusion liquid out from the infusion bag 10. If the pressure in third space 34 decreases too much during the infusion process the pressure can again be increased by means of the air pump 44.

The pressure regulator 42 provides a constant pressure in the pressure generating liquid which is carried to the flow rate regulator 40. By means of the flow rate regulator 40 the pressure generating liquid is made to flow into the second space 16 via the drip chamber 38. The second space expands and exerts a pressure on the infusion bag 10 which is thereby compressed. The infusion bag 10 in turn exerts a pressure on lid 30. This makes the connecting element 32 exert a force on the first portion 21. This force is directed in a leftward direction in FIG. 1. Thereby the load on the conduit means 12 exerted by the first 21 and the second 22 portions is decreased. When this load has decreased sufficiently infusion liquid will flow through the conduit means 12 and thus reach the patient.

Thus a state of equilibrium is established between the pressure of the infusion liquid in the infusion bag 10 and the load which the first 21 and the second 22 portions exert on the conduit means 12. Therefore the infusion liquid will be led to the patient at exactly the same flow rate as the flow rate of the pressure generating liquid prevailing between the third space 34 and the second space 16. This makes the drip rate of the pressure generating liquid in the drip chamber 38 to exactly correspond to the drip rate of the infusion liquid which is delivered to the patient.

The safety function in regard of overpressure will now be described in more detail by reference to FIGS. 2A, B and C.

Figure 2B:
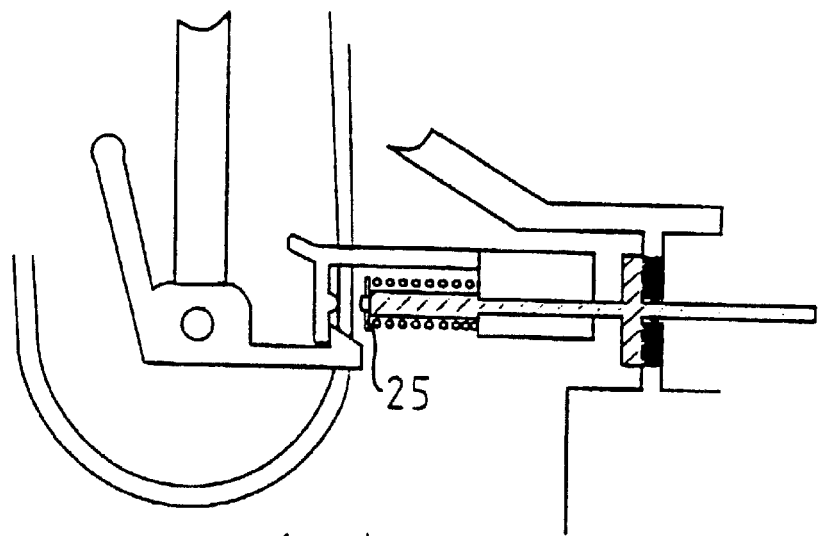

If a blockage would occur in the conduit means 12, in the infusion cannula 15 or where the infusion cannula 15 abuts an organ of the patient so as to prevent infusion liquid from flowing through the conduit means 12 the safety function in regard of overpressure is trigged. In this case the pressure on the infusion bag 10 thus increases when the pressure generating liquid flows into the second space 16. The lid 30 thereby affects the connecting element 32 in such a way so as to make the load on the conduit means 12 exerted by the first 21 and the second 22 portions to decrease. The first section 23 thereby will glide relatively to the second section 24 until the first section 23 reaches the stop face 28. This situation is shown in FIG. 2B.

Figure 2C:
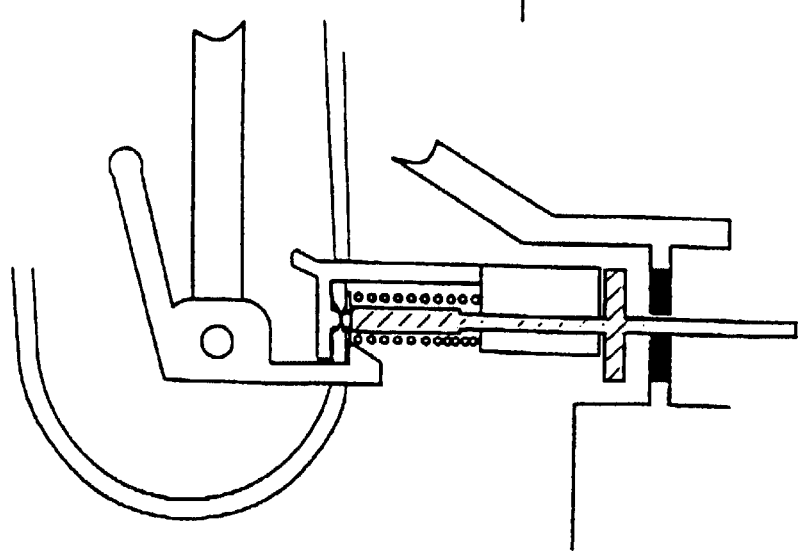

If the pressure on the infusion bag 10 continues to increase the lid 30 will increase the force on the portion 21 via the connecting element 32. The first section 23 thereby will exert a force in a leftward direction in FIGS. 2A, B and C on the second portion 22. When this force becomes sufficiently high the third section 27 will disengage from the magnet 50. Thereby the force which the first second 23 exerts on the second section 22 will cease. The spring coil 26 thereby will displace the first section 23 in a direction away from the stop face 28. The first 21 and the second 22 portions thereby will again abut on and exert pressure on the conduit means 12 to prevent infusion liquid from flowing through the conduit means. This situation is shown in FIG. 2C. According to a preferred embodiment also the third conduit 51 will be opened; this allows air to flow out from the second rubber bladder 35. Thereby the pressure in the third space 34 decreases and the infusion process is stopped.

An alternative embodiment of the invention is shown in FIG. 3. According to this embodiment the apparatus comprises a pump unit 46 which is arranged for pumping pressure generating liquid from the third space 34 to the second space 16 at a controlled pumping rate. In this context there is no need for an air pump 44. In addition no separate pressure regulator 42 or flow rate regulator 40 is required.

In this case the pump unit 46 thus makes the flow of the pressure generating liquid to proceed at a controlled rate. The second rubber bladder 35 therefore is in communication with the environment. This results in the pressure generating liquid in the third space 34 to not to be put under pressure.

The following advantages are obtained, i.a., with an infusion apparatus according to the invention. The infusion apparatus is relatively simple and cheap to manufacture. The infusion apparatus does not need to be provided with electric power since it works also with a hand-driven air pump. The use of expensive disposable components is avoided. For example, there is no need for a special drip chamber connected to the infusion bag 10 or to a conduit means 12 since a drip chamber 38 forms a permanent part of the infusion apparatus. In addition the pressure generating liquid forms a closed system between the second 16 and the third 34 space, which implies that this pressure generating liquid need not be changed between different infusion processes. The closing means 20 can be designed in a simple manner so as to make the pressure in the infusion bag 10 during the infusion to be constantly higher than the counter pressure exerted by the liquid column between the closing means 20 and the patient. This results in the drip rate being independent of the height level of the infusion cannula 15 in relation to the infusion apparatus. The infusion apparatus works reliably without complicated movable parts. The infusion apparatus can be manufactured with a low weight and therefore can be borne by a patient. The infusion apparatus can also cope with high flow rates of infusion liquid. The infusion apparatus can be used with infusion bags 10 of standard format as well as with infusion bags differing much in size since the volume of the first space 16 in which the infusion bag 10 is disposed can be varied by means of the pressure generating liquid.

The invention is not limited to the embodiments shown but can be varied and modified within the framework of the following patent claims.

What is claimed is:

1. An infusion apparatus for use in combination with an infusion bag containing an infusion liquid for transport of infusion liquid to a patient, the apparatus comprising a first space in which the infusion bag is intended to be disposed, a second space of variable volume provided with an inlet through which a pressure generating liquid can be supplied to the second space to change the volume of the second space, the first and the second spaces being arranged in such a manner that, by said volume change, the pressure generating liquid exerts a pressure on the infusion bag in the first space to make the infusion liquid leave the infusion bag via the conduit means;

a closing means designed and arranged to abut on and exert a load on the conduit means in such a manner, that infusion liquid does not flow out from the infusion bag when the pressure generating liquid is not exerting a pressure on the infusion bag, said load diminishing when the pressure generating liquid exerts a pressure on the infusion bag to make the infusion liquid leave the infusion bag via the conduit means provided that the pressure generating liquid exerts at least a certain minimum pressure on the infusion bag;

a supporting means arranged to abut the infusion bag when the infusion bag is disposed in the first space, the supporting means being arranged in such a way that, when the pressure generating liquid is exerting a pressure on the infusion bag, the bag will exert a pressure on the supporting means;

a connecting element for connecting the supporting means with the closing means to make the load which the closing means exerts on the conduit means decrease when the infusion bag exerts a pressure on the supporting means;

a third space is arranged to contain the pressure generating liquid, said space being connected with the second space by connecting means for transport of the pressure generating liquid from the third space to the second space; and the connecting means comprises a drip chamber which allows visual control of the pressure generating liquid transported from the third to the second space.

2. The infusion apparatus of claim 1, which is arranged such that, when the pressure generating liquid is exerting a pressure on the infusion bag that makes the infusion liquid leave the infusion bag via the conduit means, the flow velocity of the pressure generating liquid in the drip chamber will correspond to the flow rate of the infusion liquid in the conduit means.

3. An infusion apparatus for use in combination with an infusion bag containing an infusion liquid for transport of infusion liquid to a patient, the apparatus comprising a first space in which the infusion bag is intended to be disposed, a second space of variable volume provided with an inlet through which a pressure generating liquid can be supplied to the second space to change the volume of the second space, the first and the second spaces being arranged in such a manner that, by said volume change, the pressure generating liquid exerts a pressure on the infusion bag in the first space to make the infusion liquid leave the infusion bag via the conduit means;

a closing means designed and arranged to abut on and exert a load on the conduit means in such a manner, that infusion liquid does not flow out from the infusion bag when the pressure generating liquid is not exerting a pressure on the infusion bag, said load diminishing when the pressure generating liquid exerts a pressure on the infusion bag to make the infusion liquid leave the infusion bag via the conduit means provided that the pressure generating liquid exerts at least a certain minimum pressure on the infusion bag;

a supporting means arranged to abut the infusion bag when the infusion bag is disposed in the first space, the supporting means being arranged in such a way that, when the pressure generating liquid is exerting a pressure on the infusion bag, the bag will exert a pressure on the supporting means;

a connecting element for connecting the supporting means with the closing means to make the load which the closing means exerts on the conduit means decrease when the infusion bag exerts a pressure on the supporting means;

a third space is arranged to contain the pressure generating liquid, said space being connected with the second space by connecting means for transport of the pressure generating liquid from the third space to the second space; and the connecting means comprises a flow speed regulator to control the flow rate of the pressure generating liquid to the second space.

4. The infusion apparatus of claim 3, wherein the connecting means comprises a pressure regulator disposed between the third space and the flow rate regulator to provide a constant pressure in the pressure generating liquid present at the side of the flow speed regulator to which pressure generating liquid is supplied from the third space.

5. The infusion apparatus of claim 4, wherein the second portion is connected to a frame portion of the infusion apparatus by a joining element in such a way that, when a force exceeding a certain level is exerted on the second portion in at least one direction, the second portion will disengage from the frame portion, the safety function in regard of overpressure being arranged to be exerted by the supporting means, the connecting element, the first portion, the second portion and the joining element in combination in such a way that, as the pressure on the supporting means exceeds a certain level in spite of the supporting means via the connecting element having affected the first portion in a way so as to make the load on the connecting means decrease, the supporting means causes, by the connecting element, the first portion and the joining element, the second portion to disengage from the frame portion while the load on the conduit means again increases and the pressure on the supporting means decreases.

6. Infusion apparatus according to claim 5, wherein the joining element comprises a magnet.

* * * * *